United States Patent [19]

Neumann et al.

[11] Patent Number: 5,449,821

[45] Date of Patent: Sep. 12, 1995

[54] MULTIMETAL OXIDE COMPOSITIONS FOR GAS-PHASE CATALYTIC OXIDATION

[75] Inventors: Hans-Peter Neumann, Mannheim; Hans Martan, Frankenthal; Hermann Petersen, Gruenstadt; Walter Doerflinger, Oestringen, all of Germany

[73] Assignee: Basf Aktiengesellschaft, Ludwigshafen, Germany

[21] Appl. No.: 268,504

[22] Filed: Jun. 30, 1994

Related U.S. Application Data

[62] Division of Ser. No. 64,428, May 21, 1993, Pat. No. 5,364,825.

[30] Foreign Application Priority Data

Jun. 25, 1992 [DE] Germany .................. 42 20 859.9

[51] Int. Cl.⁶ .................................. C07C 51/16
[52] U.S. Cl. ............................ 562/546; 562/547; 562/549; 562/577; 562/598; 568/477; 568/478; 568/480
[58] Field of Search ............. 562/544, 532, 534, 535, 562/536, 546, 548, 600, 547, 549, 577, 598; 568/475, 476, 479, 477, 478, 480

[56] References Cited

U.S. PATENT DOCUMENTS 5,153,162 10/1992 Kurimoto et al. ............... 502/209
5,198,581 3/1993 Kawajiri et al. ................. 562/546

Primary Examiner—José G. Dees
Assistant Examiner—Rosalynd A. Williams
Attorney, Agent, or Firm—Oblon, Spivak, McClelland, Maier & Neustadt

[57] ABSTRACT

A process for the gas phase catalytic oxidation of a $C_{3-6}$ alkane, alkanol, alkene or alkenal using as a catalyst multimetal oxide compositions of the formula I, $[X^1_aX^2_bO_x]_p [X^3_cX^4_dX^5_eX^6_fX^7_gX^2_hO_y]_q$, where $X^1$ is bismuth, tellurium, antimony, tin and/or copper, $X^2$ is molybdenum and/or tungsten, $X^3$ is an alkali metal, thallium and/or samarium, $X^4$ is an alkaline earth metal, nickel, cobalt, copper, manganose, zinc, tin, cadmium and/or mercury, $X^6$ is iron, chromium, cerium and/or vanadium, $X^6$ is phosphorus, arsenic, boron and/or antimony, $X^7$ is a rare-earth metal, titanium, zirconium, niobium, tantalum, rhenium, ruthenium, rhodium, silver, gold, aluminum, gallium, indium, silicon, geranium, lead, thorium and/or uranium, a is from 0.01 to 8, b is from 0.1 to 30, c is from 0 to 4, d is from 0 to 20, e is from 0 to 20, f is from 0 to 6, g is from 0 to 15, h is from 8 to 16, x and y are numbers determined by the valency and frequency of the elements in I other than oxygen, and p and q are numbers whose ratio p/q is from 0.1 to 10, containing three-dimensional regions with a chemical composition $X^1_aX^2_bO_x$ which are delimited from their local environment due to their chemical composition which is different from their local environment, and whose maximum diameter is from 1 to 25 μm.

23 Claims, No Drawings

MULTIMETAL OXIDE COMPOSITIONS FOR GAS-PHASE CATALYTIC OXIDATION

This is a division of application Ser. No. 08/064,428, filed on May 21, 1993, now U.S. Pat. No. 5,364,825 on Nov. 15, 1994.

The present invention relates to compositions of the formula I $$[X^1_a X^2_b O_x]_p [X^3_c X^4_d X^5_e X^6_f X^7_g X^2_h O_y]_q \qquad (I)$$

where
- $X^1$ is bismuth, tellurium, antimony, tin and/or copper,
- $X^2$ is molybdenum and/or tungsten,
- $X^3$ is an alkali metal, thallium and/or samarium,
- $X^4$ is an alkaline earth metal, nickel, cobalt, copper, manganese, zinc, tin, cadmium and/or mercury,
- $X^5$ is iron, chromium, cerium and/or vanadium,
- $X^6$ is phosphorus, arsenic, boron and/or antimony,
- $X^7$ is a rare-earth metal, titanium, zirconium, niobium, tantalum, rhenium, ruthenium, rhodium, silver, gold, aluminum, gallium, indium, silicon, germanium, lead, thorium and/or uranium,
- a is from 0.01 to 8,
- b is from 0.1 to 30,
- c is from 0 to 4,
- d is from 0 to 20,
- e is from 0 to 20,
- f is from 0 to 6,
- g is from 0 to 15,
- h is from 8 to 16,
- x and y are numbers determined by the valency and frequency of the elements in I other than oxygen, and p and q are numbers whose ratio p/q is from 0.1 to 10, containing three-dimensional regions with a chemical composition $X^1_a X^2_b O_x$ which are delimited from their local environment due to their chemical composition which is different from their local environment, and whose maximum diameter (longest line passing through the center of gravity of the region and connecting two points on the surface (interface) of the region) is from 1 to 25 μm, preferably from 1 to 20 μm, particularly preferably from 5 to 15 μm.

The present invention also relates to a process for the preparation of these compositions, and to the use thereof (the experimental determination of the maximum diameter is carried out, for example, by energy dispersive X-ray analysis (EDXS), for example using a JEOL JCXA/733 electron beam microprobe).

Compositions of the formula I are disclosed in EP-A 835.

Concerning the preparation of these compositions, EP-A 835 recommends first preparing the mixed oxide $X^1_a X^2_b O_x$ in the absence of the other constituents of the compositions I, mixing this oxide, after its preparation, with sources of the other constituents of the compositions I, and drying and calcining the mixture.

In detail, the preparation can be carried out by preparing $X^1_a X^2_b O_x$ by precipitation in a suitable manner from solutions containing soluble compounds of the elements $X^1$ and $X^2$, grinding the precipitated product, after drying and calcination, in a ball mill, and then mixing the powder with an aqueous mixture containing the sources of the other constituents of the compositions I, and drying and calcining the mixture, or directly adding the sources of the other constituents to the slurry containing the product prepared by suitable precipitation and drying and calcining the resultant mixture.

EP-A 835 furthermore discloses employing the compositions of the formula I as catalysts for the gas-phase catalytic oxidations of organic compounds. However, the compositions of the formula I disclosed in EP-A 835 have the disadvantage of unsatisfactory activity and selectivity when used in the gas-phase catalytic oxidation of organic compounds.

DE-C 33 38 380 discloses catalytically active compositions of the formula II $$Bi_{a'} W_{b'} Fe_{c'} Mo_{d'} Y^1_{e'} Y^2_{f'} Y^3_{g'} Y^4_{h'} O_{x'} \qquad (II)$$

where
- $Y^1$ is nickel and/or cobalt,
- $Y^2$ is thallium, an alkali metal and/or an alkaline earth metal,
- $Y^3$ is phosphorus, arsenic, boron, antimony, tin, cerium, lead and/or niobium,
- $Y^4$ is silicon, aluminum, zirconium and/or titanium,
- d' is 12,
- a' is from 0.5 to 5
- b' is from 0.5 to 4 } where a'/b' = 0.1 to 4,
- c' is from 0.2 to 5,
- e' is from 3 to 10,
- f' is from 0.02 to 2,
- g' is from 0 to 5,
- h' is from 0 to 10, and
- x' is a number determined by the valency and frequency of the elements in II other than oxygen, which are obtained by first mixing a bismuth compound and a tungsten compound in an aqueous medium, drying the aqueous mixture, calcining the resultant composition at from 600° to 900° C. and subsequently powdering the calcined composition so that the particle size is less than 152 μm, mixing the resultant powder with an aqueous solution of the sources of the other constituents of the composition II, evaporating the resultant mixture and shaping and calcining the residue.

DE-C 33 38 380 also discloses that the compositions II are suitable as catalysts for the preparation of unsaturated aldehydes by gas-phase catalytic oxidation.

However, the compositions II disclosed in DE-C 33 38 380 have the disadvantage of unsatisfactory activity and selectivity when used for the preparation of unsaturated aldehydes by gas-phase catalytic oxidation.

It is an object of the present invention to provide compositions of the formula I which have increased activity and selectivity as catalysts for the gas-phase catalytic oxidation of organic compounds, in particular for the preparation of unsaturated aldehydes and unsaturated carboxylic acids by gas-phase catalytic oxidation.

We have found that this object is achieved by the compositions defined at the outset.

Preferred compositions I are those which contain at least one of the elements iron, chromium, cerium, vanadium and another rare-earth metal having a stoichiometric coefficient other than 0, advantageously ≧0.01.

Particularly advantageous compositions I according to the invention are those in which $X^1$ is bismuth. Of these, those are in turn preferred which have the formula III $$[Bi_{a''} Z^2_{b''} O_{x''}]_{p''} [Z^2_{12} Z^3_{c''} Z^4_{d''} Fe_{e''} Z^5_{f''} Z^6_{g''} Z^7_{h''} O_{y''}]_{q''} \qquad (III)$$

where

Z$^2$ is molybdenum and/or tungsten,

Z$^3$ is nickel and/or cobalt,

Z$^4$ is thallium, an alkali metal and/or an alkaline earth metal,

Z$^5$ is phosphorus, arsenic, boron, antimony, tin, cerium and/or lead,

Z$^6$ is silicon, aluminum, titanium and/or zirconium,

Z$^7$ is copper, silver and/or gold, a'' is from 0.1 to 1, b'' is from 0.2 to 2, c'' is from 3 to 10, d'' is from 0.02 to 2, e'' is from 0.01 to 5, preferably from 0.1 to 3, f'' is from 0 to 5, g'' is from 0 to 10, h'' is from 0 to 1, x'' and y'' are numbers determined by the valency and frequency of the elements in III other than oxygen, and p'' and q'' are numbers whose ratio p''/q'' is from 0.1 to 5, preferably from 0.5 to 2, very particularly preferred compositions III being those in which Z$^2_{b''}$ is (tungsten)$_{b''}$ and Z$^2_{12}$ is (molybdenum)$_{12}$.

It is furthermore advantageous if at least 50 mol % (preferably 100 mol %) of all the [X$^1_a$X$^2_b$O$_p$ ([Bi$_{a''}$Z$^2_{b''}$O$_{x''}$]$_{p''}$) of the compositions I (compositions III) according to the invention is in the form of three-dimensional regions with the chemical composition X$^1_a$X$^2_b$O$_x$ (Bi$_{a''}$Z$^2_{b''}$O$_{x''}$) which are delimited from their local environment due to their chemical composition which is different from their local environment, and whose maximum diameter is in part in the range from 1 to 25 $\mu$m (preferably from 1 to 20 $\mu$m, particularly preferably from 5 to 15$\mu$m).

The higher the percentage of the number of the various maximum diameters (based on the total number of regions present) which has a value in the range from 1 to 25 $\mu$m (preferably from 1 to 20 $\mu$m, particularly preferably from 5 to 15 $\mu$m), the more advantageous are the compositions according to the invention.

It is preferred for at least half the maximum diameters to be in the range from 1 to 25 $\mu$m (advantageously in the range from 1 to 20 $\mu$m, particularly preferably from 5 to 15 $\mu$m), and it is very particularly preferred for all the maximum diameters to be in this range.

The compositions I according to the invention are obtainable in a particularly suitable manner, for example, by first preparing a calcined mixed oxide X$^1_a$X$^1_b$O$_x$ in a manner known per se (cf. EP-A 835 and DE-C 33 38 380), (for example by mixing water-soluble salts of X$^1$, such as nitrates, carbonates, hydroxides or acetates, with X$^2$-acids or ammonium salts thereof in water, drying (preferably spray drying) the mixture and calcining the dried composition), comminuting the oxide (for example in a ball mill or by jet grinding), separating the particle class having a maximum particle diameter in the maximum diameter range desired for the composition I from the resultant powder, generally comprising substantially spherical particles, by a known classification method (for example wet or dry screening), and preferably mixing this particle class with, preferably, from 0.1 to 3% by weight, based on the weight of this separated particle class, of finely divided SiO$_2$ (the number average maximum particle diameter of the SiO$_2$ particles, which are usually substantially spherical, is expediently from 10 to 50 nm), giving a starting composition I.

The calcined mixed oxide prepared first advantageously has the stoichiometry BiZ$^2$O$_6$, Bi$_2$Z$^2_2$O$_9$ and/or Bi$_2$Z$^2_3$O$_{12}$, of which Bi$_2$Z$^2_2$O$_6$ is preferred, in particular if Z$^2$ is tungsten.

The calcination temperature is expediently from 400° to 900° C., preferably from 600° to 900° C. The calcination is usually carried out in a stream of air. The calcination duration is generally a few hours.

A very intimate, preferably finely divided dry mixture of the other constituents of the desired composition according to the invention is prepared starting from sources which are suitable in a manner known per se (cf. EP-A 835 and DE-C 33 38 380) (for example water-soluble salts such as halides, nitrates, acetates, carbonates or hydroxides are combined in an aqueous solution, and the aqueous solution is subsequently spray-dried, or water-insoluble salts, for example oxides, are suspended in an aqueous medium and the suspension is subsequently spray-dried). This dry mixture is referred to here as starting composition 2. The only essential feature is that the constituents of the starting composition 2 are either already oxides or are compounds which can be converted into oxides by heating, if necessary in the presence of oxygen.

The starting composition 1 and starting composition 2 are subsequently mixed with one another in the desired mixing ratio, preferably compacted by pressing, and then calcined (normally in a stream of air) for several hours, expediently at from 400° to 600° C. In a less preferred embodiment, the calcined mixed oxide X$^1_a$X$^2_b$O$_x$ formed initially can be intimately mixed with sources of the remaining constituents of the desired composition according to the invention, also in a liquid, preferably aqueous, medium. This mixture is subsequently dried to give an intimate dry mix, and then, as described above, calcined, in shaped or reshaped form. The sources of the remaining constituents can be in dissolved and/or suspended form in this liquid medium, whereas the calcined mixed oxide formed initially should be essentially insoluble in this liquid medium, i.e. must be in suspended form.

In the case of unsupported catalysts, the pressing preferably gives the desired catalyst geometry directly, preference being given to hollow cylinders having an external diameter and a length of from 2 to 10 mm and a wall thickness of from 1 to 3 mm. However, the active composition I according to the invention can also be comminuted after calcination and applied to inert supports to prepare supported catalysts. The application can also be carried out before the final calcination. In this case, the application is preferably carried out as described in EP-B 293 859. It is of course also possible for the compositions according to the invention to be employed in powder form.

The compositions according to the invention are particularly suitable as catalysts of increased activity and selectivity for the gas-phase catalytic oxidation of organic compounds, such as lower (C$_3$—C$_6$)alkanes, alkanols, alkanals, alkenes and alkenals, to give olefinically unsaturated aldehydes and/or carboxylic acids, and the corresponding nitriles (ammonoxidation, mainly of propene to give acrylonitrile and of 2-methylpropene or tert-butanol to give methacrylonitrile). They are, however, also suitable for oxidative dehydrogenation of organic compounds.

The compositions according to the invention, in particular the compositions III, are particularly suitable for the preparation of acrolein, acrylic acid, methacrolein and methacrylic acid by gas-phase catalytic oxidation, the starting compounds employed preferably being propene, 2-methylpropene or tert-butanol. The compositions according to the invention are particularly advantageous as catalysts for the preparation of acrolein and methacrolein.

The oxidant used, in a manner known per se, is oxygen, expediently diluted with inert gases. Examples of suitable inert gases are $N_2$ and steam. The reaction temperature and pressure are known to persons skilled in the art.

EXAMPLES a) Preparation of the starting compositions 1

6.7 kg of $H_2WO_4$ were added to 50 kg of a solution of $Bi(NO_3)_3$ in aqueous nitric acid (11% by weight of Bi, 6.4% by weight of $HNO_3$, in each case based on the solution), and the mixture was stirred at 50° C. for 1 hour.

The resultant suspension was spray-dried and calcined at 750° C. for 2 hours. The calcined mixed oxide prepared in this way ($Bi_2W_2O_9$ with a small amount of $WO_3$ impurity) was ground and classified in the following maximum particle diameter (d) fractions:

| | |
|---|---|
| VF1: | 0.1 μm < d ≦ 1 μm |
| F2: | 1 μm < d ≦ 5 μm |
| F3: | 5 μm < d ≦ 10 μm |
| F4: | 10 μm < d ≦ 15 μm |
| F5: | 15 μm < d ≦ 20 μm |
| F6: | 20 μm < d ≦ 25 μm |
| VF7: | 30 μm < d ≦ 50 μm |
| VF8: | 90 μm < d ≦ 120 μm |

All fractions were then mixed with 1% of their weight of finely divided (number average maximum diameter 28 nm) $SiO_2$.

b) Preparation of a starting composition 2

A solution of 85.5 kg of ammonium molybdate in 240 l of water was mixed with a solution containing 11.9 kg of cobalt(II) nitrate and 5.7 kg of iron(III) nitrate dissolved in 80 l of water, and with 7.8 kg of an aqueous mixture containing 20% of its weight of colloidal $SiO_2$ and with 377 g of an aqueous solution containing 48% by weight of KOH. The mixture was subsequently stirred for 3 hours, and the resultant aqueous suspension was spray-dried.

c) Preparation of compositions I

The various fractions VF1 to VF8 containing finely divided $SiO_2$ were each mixed separately with the starting composition 2 in the amount necessary for a composition I of the composition

$[Bi_2W_2O_9]_{0.5}Mo_{12}Co_5Fe_{2.5}Si_{1.6}K_{0.05}O_x$, the mixture was pressed to give hollow cylinders with a length of 5 mm, an external diameter of 5 mm and a wall thickness of 1.5 mm, and the cylinders were subsequently calcined in a stream of air at 470° C. for 6 hours. Analysis of the resultant composition I by energy dispersive X-ray analysis (EDXS) using a JEOL JCXA/733 electron beam microprobe showed that the resultant compositions I contain three-dimensional regions with the chemical composition $Bi_2W_2O_9$ which are delimited from their local environment due to their chemical composition which is different from their local environment, and whose maximum diameter essentially corresponds to the maximum particle diameters of the particle fractions VF1 to VF8 used for their preparation.

d) Gas-phase catalytic oxidation of propene

A reaction tube (V2A, wall thickness 2 mm, internal diameter 25 mm, salt-bath temperature control) filled in each case with 1200 ml of the respective composition I from c) was charged with 2400 l (S.T.P.)/h of a gas mixture having the composition 5% by volume of propene, 9% by volume of oxygen and 86% by volume of nitrogen.

The salt-bath temperature was in all cases adjusted so that a propene conversion of about 98 mol % resulted for a single pass.

The salt-bath temperatures (measure of the activity of the composition I employed) necessary in this respect are a function of the fractions VF1 to VF8 used for the preparation of the employed composition I in the form of the particular starting composition 1, and the resultant selectivities (based on the total amount of acrolein and acrylic acid formed) are shown by the Table.

TABLE

| | Propene conversion [mol %] | Salt-bath temperature [°C.] | Selectivity [mol %] |
|---|---|---|---|
| VF1 | 98 | 350 | 95.8 |
| F2 | 97.9 | 338 | 96.8 |
| F3 | 98.1 | 330 | 96.3 |
| F4 | 97.9 | 322 | 95.7 |
| F5 | 98.0 | 322 | 95.0 |
| F6 | 97.9 | 337 | 94.3 |
| VF7 | 98.0 | 355 | 93.8 |
| VF8 | 98.0 | 382 | 90.8 |

As can be seen, both the activity and the selectivity pass through a pronounced maximum. If the two parameters are combined, particularly advantageous compositions I are found to be those in which the maximum diameter of the chemically delimited regions present therein with the composition $Bi_2W_2O_9$ are exclusively in the range from 1 to 25 μm.

After an operating time of 500 hours, the compositions I employed in each case were again subjected to energy dispersive X-ray analysis. This showed that the chemically delimited regions with the composition $Bi_2W_2O_9$ were essentially unchanged with respect to their maximum diameter.

We claim:

1. A process for the gas-phase catalytic oxidation of a $C_{3-6}$ alkane, alkanol, alkene or alkenal, comprising the step of:

contacting said $C_{3-6}$ alkane, alkanol, alkene or alkenal with a catalyst;

wherein said catalyst has a composition of the formula I:

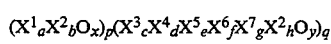
$(X^1_aX^2_bO_x)_p(X^3_cX^4_dX^5_eX^6_fX^7_gX^2_hO_y)_q$ where $X^1$ is bismuth, tellurium, antimony, tin and/or copper;

$X^2$ is molybdenum and/or tungsten;

$X^3$ is an alkai metal, thallium and/or samarium;

$X^4$ is an alkaline earth metal, nickel, cobalt, copper, manganese, zinc, tin, cadmium, and/or mercury;

$X^5$ is iron, chromium, cerium and/or vanadium;

$X^6$ is phosphorus, arsenic, boron and/or antimony;

$X^7$ is a rare-earth metal, titanium, zirconium, niobium, tantalum, rhenium, ruthenium, rhodium, silver, gold, aluminum, gallium, indium, silicon, germanium, lead, thorium and/or uranium;

a is from 0.01 to 8;
b is from 0.1 to 30;
c is from 0 to 4;
d is from 0 to 20;
e is from 0 to 20;
f is from 0 to 6;
g is from 0 to 15;
h is from 8 to 16;
x and y are numbers determined by the valency and frequency of the elements in formula I other than oxygen, and p and q are numbers whose ratio p/q is from 0.1 to 10, containing three-dimensional regions with a chemical formula $X^1_a X^2_b O_x$ and a local environment, wherein said regions are delimited from said local environment due to said chemical formula of said regions which is different from said local environment, wherein at least 50% of said regions have a maximum diameter of from 1 to 25 μm.

2. A process for gas-phase catalytic oxidation of a $C_{3-6}$ alkane, alkanol, alkene or alkenal as in claim 1, wherein said regions contain all the $(X^1_a X^2_b O_x)_p$ as $X^1_a X^2_b O_x$.

3. A process for gas-phase catalytic oxidation of a $C_{3-6}$ alkane, alkanol, alkene or alkenal as in claim 1, wherein all the locally delimited regions with the chemical formula $(X^1_a X^2_b O_x)$ have a maximum diameter in the range of from 1 to 25 μm.

4. A process for gas-phase catalytic oxidation of a $C_{3-6}$ alkane, alkanol, alkene or alkenal as in claim 2, wherein all the locally delimited regions with the chemical formula $(X^1_a X^2_b O_x)$ have a maximum diameter in the range of from 1 to 25 μm.

5. A process for gas-phase catalytic oxidation of a $C_{3-6}$ alkane, alkanol, alkene or alkenal as in claim 1, wherein $X^1$ is bismuth.

6. A process for gas-phase catalytic oxidation of a $C_{3-6}$ alkane, alkanol, alkene or alkenal as in claim 2, wherein $X^1$ is bismuth.

7. A process for gas-phase catalytic oxidation of a $C_{3-6}$ alkane, alkanol, alkene or alkenal as in claim 1, wherein $X^1_a X^2_b O_x$ is identical with $Bi_2 W_2 O_9$.

8. A process for gas-phase catalytic oxidation of a $C_{3-6}$ alkane, alkanol, alkene or alkenal as in claim 2, wherein $X^1_a X^2_b O_x$ is identical with $Bi_2 W_2 O_9$.

9. A process for gas-phase catalytic oxidation of a $C_{3-6}$ alkane, alkanol, alkene or alkenal as in claim 3, wherein $X^1$ is bismuth.

10. A process for gas-phase catalytic oxidation of a $C_{3-6}$ alkane, alkanol, alkene or alkenal as in claim 4, wherein $X^1$ is bismuth.

11. A process for gas-phase catalytic oxidation of a $C_{3-6}$ alkane, alkanol, alkene or alkenal as In claim 3, wherein $X^1_a X^2_b O_x$ is identical with $Bi_2 W_2 O_9$.

12. A process for gas-phase catalytic oxidation of a $C_{3-6}$ alkane, alkanol, alkene or alkenal as in claim 4, wherein $X^1_a X^2_b O_x$ is identical with $Bi_2 W_2 O_9$.

13. A process for gas-phase catalytic oxidation of a $C_{3-6}$ alkane, alkanol, alkene or alkenal as in claim 5, where $X^1_a X^2_b O_x$ is identical with $Bi_2 W_2 O_9$.

14. A process for gas-phase catalytic oxidation of a $C_{3-6}$ alkane, alkanol, alkene or alkenal as in claim 6, wherein $X^1_a X^2_b O_x$ is identical with $Bi_2 W_2 O_9$.

15. A process for gas-phase catalytic oxidation of a $C_{3-6}$ alkane, alkanol, alkene or alkenal as in claim 9, wherein $X^1_a X^2_b O_x$ is identical with $Bi_2 W_2 O_9$.

16. A process for gas-phase catalytic oxidation of a $C_{3-6}$ alkane, alkanol, alkene or alkenal as in claim 10, wherein $X^1_a X^2_b O_x$ is identical with $Bi_2 W_2 O_9$.

17. A process for gas-phase catalytic oxidation of a $C_{3-6}$ alkane, alkanol, alkene or alkenal as in claim 1, wherein said alkene is propene.

18. A process for gas-phase catalytic oxidation of a $C_{3-6}$ alkane, alkanol, alkene or alkenal as in claim 15, wherein said alkene is propene.

19. A process for gas-phase catalytic oxidation of a $C_{3-6}$ alkane, alkanol, alkene or alkenal as in claim 1, wherein said alkene is 2-methylpropene.

20. A process for gas-phase catalytic oxidation of a alkane, alkanol, alkene or alkenal as in claim 15, wherein said alkene is 2-methylpropene.

21. A process for gas-phase catalytic oxidation of a $C_{3-6}$ alkane, alkanol, alkene or alkenal, comprising the step of:

contacting said alkane, alkanol, alkene or alkenal with a catalyst;
wherein said catalyst has a composition of the formula I:

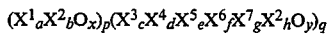

where
$X^1$ is bismuth, tellurium, antimony, tin and/or copper;
$X^2$ is molybdenum and/or tungsten;
$X^3$ is an alkali metal, thallium and/or samarium;
$X^4$ is an alkaline earth metal, nickel, cobalt, copper, manganese, zinc, tin, cadmium, and/or mercury;
$X^5$ is iron, chromium, cerium and/or vanadium;
$X^6$ is phosphorus, arsenic, boron and/or antimony;
$X^7$ is a rare-earth metal, titanium, zirconium, niobium, tantalum, rhenium, ruthenium, rhodium, silver, gold, aluminum, gallium, indium, silicon, germanium, lead, thorium and/or uranium;
a is from 0.01 to 8;
b is from 0.1 to 30;
c is from 0 to 4;
d is from 0 to 20;
e is from 0 to 20;
f is from 0 to 6;
g is from 0 to 15;
h is from 8 to 16;
x and y are numbers determined by the valency and frequency of the elements in formula I other than oxygen, and p and q are numbers whose ratio p/q is from 0.1 to 10, synthesized by preparing a first finely divided powder from a calcined mixed oxide $X^1_a X^2_b O_x$, wherein said mixed oxide has a maximum particle diameter in the range from 1 to 25 μm, preparing a second finely divided powder containing $X^3$, $X^4$, $X^5$, $X^6$, $X^7$ and $X^2$, wherein said second powder is in a form which is already oxidic and/or can be converted into oxidic form by calcination, mixing said first and said second powder to form a mixture, and calcining said mixture.

22. A process for gas-phase catalytic oxidation of a $C_{3-6}$ alkane, alkanol, alkene or alkenal as in claim 21, wherein said alkene is propene.

23. A process for gas-phase catalytic oxidation of a alkane, alkanol, alkene or alkenal as in claim 21, wherein said alkene is 2-methylpropene.

* * * * *